United States Patent
Schneider et al.

(10) Patent No.: US 10,829,746 B2
(45) Date of Patent: Nov. 10, 2020

(54) METHOD FOR THE FERMENTATIVE PRODUCTION OF L-LYSINE

(71) Applicant: Evonik Operations GmbH, Essen (DE)

(72) Inventors: Frank Schneider, Halle (DE); Georg Thierbach, Bielefeld (DE); Kornelia Voß, Steinhagen (DE); Thomas Bekel, Halle (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/718,779

(22) Filed: Dec. 18, 2019

(65) Prior Publication Data
US 2020/0231946 A1    Jul. 23, 2020

(30) Foreign Application Priority Data

Jan. 23, 2019  (EP) .................................... 19153243

(51) Int. Cl.
| | | |
|---|---|---|
| C12P 13/08 | (2006.01) | |
| C12N 1/21 | (2006.01) | |
| C12N 9/12 | (2006.01) | |
| C12P 21/00 | (2006.01) | |

(52) U.S. Cl.
CPC ............ C12N 9/1217 (2013.01); C12P 21/00 (2013.01); C12Y 207/02004 (2013.01)

(58) Field of Classification Search
None
See application file for complete search history.

(56) References Cited

U.S. PATENT DOCUMENTS

| 8,697,850 B2 | 4/2014 | Jessberger et al. |
| 9,422,568 B2 | 8/2016 | Jessberger et al. |
| 2009/0311758 A1 | 12/2009 | Jessberger et al. |
| 2010/0192985 A1* | 8/2010 | Aehle ................ C11D 3/38645 134/26 |
| 2014/0127787 A1 | 5/2014 | Jessberger et al. |

FOREIGN PATENT DOCUMENTS

| EP | 1 172 437 | 1/2002 |
| WO | 2008/092956 | 8/2008 |
| WO | 2009/141330 | 11/2009 |
| WO | 2011/158975 | 12/2011 |

OTHER PUBLICATIONS

Extended European Search Report dated May 26, 2020 in European Application No. 20150927.0, 7 pages.
Extended European Search Report dated May 21, 2019 in European Application No. 19153243.1, 7 pages.
Database Geneseq [Online] "Corynebacterium glutamicum HA protein sequence Seq ID No. 226.", XP002790673, retrieved from EBI accession No. GSP:AAB79135, Abstract, 2 pages, 2007.
Ikeda et al., J Ind Microbiol Biotechnol (2006) 33: 610-615, DOI: 10.1007/s10295-006-0104-5.
Ohnishi et al, Appl Microbiol Biotechnol (2002) 58:217-223, DOI: 10.1007/s00253-001-0883-6.

* cited by examiner

*Primary Examiner* — David Steadman
(74) *Attorney, Agent, or Firm* — Grüneberg and Myers PLLC

(57) ABSTRACT

A bacterium of the species *Corynebacterium glutamicum* has the ability to excrete L-lysine, and contains in its chromosome a polynucleotide encoding a mutated polypeptide having the assumed function of an acyltransferase, hydrolase, alpha/beta hydrolase or of a pimeloyl-ACP methyl ester esterase. Also, a method is used for producing L-lysine using such bacterium.

9 Claims, No Drawings
Specification includes a Sequence Listing.

METHOD FOR THE FERMENTATIVE PRODUCTION OF L-LYSINE

CROSS-REFERENCE TO RELATED APPLICATION

The present application claims the benefit to the European application EP 19153243.1, filed on Jan. 23, 2019, which is hereby incorporated by reference in its entirety.

REFERENCE TO A SEQUENCE LISTING

The present application is accompanied by an ASCII text file as a computer readable form containing the sequence listing, titled "Sequence-Listing-as-filed.txt," created on Dec. 16, 2019, with the file size of 39,704 bytes, which is hereby incorporated by reference in its entirety. Applicants hereby state that the information recorded in computer readable form is identical to the written (on paper or compact disc) sequence listing.

BACKGROUND OF THE INVENTION

Field of the Invention

The present invention concerns a bacterium of the species *Corynebacterium glutamicum*, having the ability to excrete L-lysine, containing in its chromosome a polynucleotide encoding a mutated polypeptide having the assumed function of an acyltransferase, hydrolase, alpha/beta hydrolase or of a pimeloyl-ACP methyl ester esterase and a method for producing L-lysine using such bacterium.

Discussion of the Background

L-lysine is used in human medicine, in the pharmaceutical industry, in the food industry and particularly in nutrition of animals. L-lysine is produced by fermentation of strains of the species *Corynebacterium glutamicum*. The methods used for improving the performance properties of these microorganisms are those of mutagenesis, selection and screening of mutants. Methods of recombinant DNA technology have likewise been used for a number of years for improvement of L-lysine-producing strains of the species *Corynebacterium glutamicum*, by modifying, i.e. enhancing or attenuating, individual genes involved in L-lysine biosynthesis and investigating the effect on L-lysine production.

The nucleotide sequences of the chromosomes of various bacteria or strains resp. of the species *Corynebacterium glutamicum*, and their analysis have been disclosed. This information is available at publicly accessible data bases and may be used for strain development purposes. One such data base is the GenBank data base of the NCBI (National Center for Biotechnology Information, U.S. National Library of Medicine 8600 Rockville Pike, Bethesda Md., 20894 USA). During the annotation procedure for a sequenced chromosome of an organism identified structures such as e. g. genes or coding sequences are furnished with a unique identifier called locus_tag by the supplier of the information to the data base.

The nucleotide sequence of the *Corynebacterium glutamicum* ATCC13032 chromosome and its analysis were described by Ikeda and Nakagawa (Applied Microbiology and Biotechnology 62, 99-109(2003)) and in EP1108790 A2. The information is available at the NCBI under accession number NC 003450.

The locus_tag NCgl0292 identifies a nucleotide sequence coding for a polypeptide being a member of the alpha/beta hydrolase superfamily. The EC number is given as 3.3.2.9. It is further predicted that the gene product is a hydrolase or an acyltransferase. The amino acid sequence of the polypeptide having a length of 331 amino acids is also available under the identifier NP 599549.

The nucleotide sequence of the *Corynebacterium glutamicum* ATCC13032 chromosome and its analysis were independently described by Kalinowski et al. (Journal of Biotechnology 104 (1-3), 5-25 (2003)). The information is available at the NCBI under accession number NC_006958. Locus_tag CGTRNA_RS01565 identifies a nucleotide sequence coding for a predicted alpha/beta hydrolase. The old_locus_tag designation cg0358 is also used in the art. The amino acid sequence of the polypeptide having a length of 331 amino acids is also available under the identifier WP 011013543.

The nucleotide sequences of locus_tag NCgl0292 and CGTRNA_RS01565 are identical.

The nucleotide sequence of the *Corynebacterium glutamicum* R chromosome and its analysis was described by Yukawa et al. (Microbiology 153(4): 1042-1058 (2007)). It is available at the NCBI under accession number AP009044. Locus_tag cgR_0383 identifies a nucleotide sequence coding for a hypothetical protein. The amino acid sequence of the polypeptide having a length of 331 amino acids is also available under the identifier BAF53347. The region from position 54 to 329 of the amino acid sequence is called MhpC and a function prediction as pimeloyl-ACP methyl ester carboxyesterase is given.

The gene mhpC (mnemonic for m-hydroxyphenylpropionic acid) of *Escherichia coli* encodes an enzyme participating in the degradation of m-hydroxyphenylpropionic acid (Ferrandez et al., Journal of Bacteriology 179(8), 2573-2581 (1997)). The enzyme is a hydrolase acting on C—C bonds and called 2-hydroxy-6-oxononatrienedioate hydrolase. The EC number is EC 3.7.1.14.

The nucleotide sequence of the *Corynebacterium glutamicum* R chromosome and its analysis is also available under accession number NC_009342. Under locus_tag designation CGR_RS01990 and old_locus_tag cgR_0383a nucleotide sequence coding for a predicted alpha/beta hydrolase is given.

S. Binder (Schriften des Forschungszentrums Jillich, Vol. 65, 2013; ISSN 1866-1875) observed an amino acid exchange A95V in the polypeptide identified by NCgl0292 after screening for improved L-lysine producers of *Corynebacterium glutamicum*.

The amino acid sequence of the polypeptide identified by locus_tag NCgl0292 (strain ATCC13032) is >97% identical to the amino acid sequence of the polypeptide identified by locus_tag cg_0383 (strain R).

Information concerning transcription signals in *Corynebacterium glutamicum*, e.g. −10 region of a promoter, or transcriptional start site (TSS) of the gene identified by old_locus_tag cg0358 can be found in Pfeifer-Sancar et al. (BMC Genomics 14:888 (2013)), Albersmeier et al. (Journal of Biotechnology 257 (2017) 99-109) or Menz et al. (BMC Genomics 2013, 14:714).

SEQ ID NO: 1 shows the nucleotide sequence corresponding to NCgl0292. SEQ ID NO: 2 shows the amino acid sequence of the NCgl0292 polypeptide.

With respect to the function of the polypeptide the art makes function predictions concerning the polypeptide shown in SEQ ID NO:2 or the homologue of strain R as acyltransferase, hydrolase, alpha/beta hydrolase and pimeloyl-ACP methyl ester esterase.

An acyltransferase is a type of transferase enzyme that acts on acyl groups. According to the Recommendations of the Nomenclature Committee of the International Union of Biochemistry and Molecular Biology (NC-IUBMB) acyltransferases are classified under EC 2.3. A review on acyltransferases is given by A. Röttig and A. Steinbüchel (Microbiology and Molecular Biology Reviews 77(2), 277-321, 2013).

A hydrolase is a type of enzyme that uses water to break a chemical bond. According to NC-IUBMB hydrolases are classified under EC 3. Hydrolases acting ester bonds (esterases) are summarized under enzyme class EC 3.1.

The term alphabeta hydrolase summarizes a group of hydrolytic enzymes characterized by the α/β hydrolase fold in the enzyme core (Ollis et al., Protein Engineering 1992; 5(3): 197-211). Said core is characterized by an alpha/beta sheet comprising eight beta sheets connected by alpha helices.

The enzyme pimeloyl-ACP methyl ester esterase (EC 3.1.1.85) of *Escherichia coli* catalyzes the hydrolysis of the methyl ester bond of pimeloyl-ACP methyl ester (ACP=acyl carrier protein) or pimeloyl-CoA methyl ester (CoA=coenzyme A) to give pimeloyl-ACP or pimeloyl-CoA. These compounds are intermediates in the biosynthesis of biotin. In *Escherichia coli* said pimeloyl-ACP methyl ester esterase polypeptide is encoded by a gene called bioH.

A conserved domain search using the BLAST (basic local alignment search tool) algorithm provided by the NCBI of the polypeptide encoded by NCgl0292 (see also SEQ ID NO:2) reveals a single specific hit matching the conserved protein domain family MhpC (identifier COG0596). This family is also referred to as pimeloyl ACP methyl ester carboxylesterase in the database.

A summary of the biotin synthesis pathway in *Escherichia coli* was given by Lin et al. (Nature Chemical Biology 6, 682-688 (2010)). A summary of enzymes of the biosynthesis of biotin present in *Corynebacterium glutamicum* is given by L. Eggeling and M. Bott (Eds.) in the Handbook of *Corynebacterium glutamicum* (CRC Press, Taylor & Francis Group. Boca Raton, US, 2005).

SUMMARY OF THE INVENTION

Object of the present invention is to provide new measures for the fermentative production of L-lysine by bacteria of the species *Corynebacterium glutamicum*.

The object underlying the invention is achieved by the subject matter of following various embodiments.
1. A bacterium of the species *Corynebacterium glutamicum* having the ability to excrete L-lysine containing in its chromosome a polynucleotide encoding a polypeptide comprising the amino acid sequence of SEQ ID NO:2, wherein the amino acid serine at position 225 is substituted by a different proteinogenic amino acid.
2. The bacterium according to embodiment 1, wherein said amino acid at position 225 of the amino acid sequence of SEQ ID NO:2 is cysteine.
3. The bacterium according to embodiment 2, wherein the polynucleotide encoding said amino acid sequence comprises the nucleotide sequence of positions 328 to 1320 of SEQ ID NO:1 with the nucleobase at position 1001 being guanine.
4. The bacterium according to embodiment 2, wherein the polynucleotide encoding said amino acid sequence comprises the nucleotide sequence of positions 328 to 1323 of SEQ ID NO:1 with the nucleobase at position 1001 being guanine.
5. The bacterium according to any of the preceding embodiments containing at least one copy of a polynucleotide coding for a feedback resistant aspartokinase polypeptide.
6. The bacterium according to embodiment 5, wherein the amino acid sequence of said feedback resistant aspartokinase polypeptide comprises the amino acid sequence of SEQ ID NO: 6 containing isoleucine at position 311 instead of threonine.
7. A method for the fermentative production of L-lysine comprising the steps of a) cultivating the bacterium as defined in any of embodiments 1 to 6 in a suitable medium under suitable conditions, and b) accumulating L-lysine in the medium to form an L-lysine containing fermentation broth.
8. The method according to embodiment 7 further comprising the step of L-lysine purification.
9. The method according to embodiment 8, wherein said purification step is selected from the group consisting of treatment with activated carbon, ionic exchange and crystallization.

DETAILED DESCRIPTION OF THE INVENTION

Accordingly, the present invention provides a bacterium of the species *Corynebacterium glutamicum*, having the ability to excrete L-lysine, containing in its chromosome a polynucleotide encoding a polypeptide comprising the amino acid sequence of SEQ ID NO:2 (i.e. NCgl0292), wherein the amino acid serine at position 225 is substituted by a different proteinogenic amino acid, preferably by cysteine ("NCgl0292 (S225C)").

The amino acid sequence shown in SEQ ID NO:2, wherein the amino acid serine at position 225 is substituted by cysteine, is identical to the amino acid shown in SEQ ID NO:4.

It was found that the bacteria modified according to the invention excreted L-lysine, into a suitable medium under suitable fermentation conditions in an increased manner as compared to a bacterium that is unmodified with respect to NCgl0292.

In a preferred embodiment the bacterium according to the invention contains in its chromosome a polynucleotide comprising the nucleotide sequence of positions 328 to 1320 of SEQ ID NO:1 with the nucleobase at position 1001 being guanine. The nucleotide sequence of positions 328 to 1320 of SEQ ID NO:1 with the nucleobase at position 1001 being guanine is identical to the nucleotide sequence of positions 328 to 1320 of SEQ ID NO:3.

In another preferred embodiment the bacterium according to the invention contains in its chromosome a polynucleotide comprising the nucleotide sequence of positions 328 to 1323 of SEQ ID NO:1 with the nucleobase at position 1001 being guanine. The nucleotide sequence of positions 328 to 1323 of SEQ ID NO:1 with the nucleobase at position 1001 being guanine is identical to the nucleotide sequence of positions 328 to 1323 of SEQ ID NO:3.

The term L-lysine, where mentioned herein, in particular in the context of product formation, also comprises their ionic forms and salts, for example L-lysine mono hydrochloride or L-lysine sulfate.

For practicing the present invention L-lysine excreting bacteria of the species *Corynebacterium glutamicum* are used. Suitable strains of *Corynebacterium glutamicum* are L-lysine excreting strains obtained from wild strains of this species for example strain ATCC13032.

Strain ATCC13032 (also available as DSM20300) is the taxonomic type strain of the species *Corynebacterium glutamicum*. Strain ATCC14067 (also available as DSM20411) is also known under the outdated designation *Brevibacterium flavum*. Strain ATCC13869 (also available as DSM1412) is also known under the outdated designation *Brevibacterium lactofermentum*.

L-lysine excreting strains of the species *Corynebacterium glutamicum* typically contain a polynucleotide coding for a feedback resistant aspartokinase polypeptide variant. A feedback resistant aspartokinase polypeptide variant means an aspartokinase which is less sensitive, or desensitized respectively, to inhibition by mixtures of L-lysine and L-threonine, e.g. 10 mM each, or mixtures of the L-lysine analogue S-(2-aminoethyl)-L-cysteine and L-threonine, e.g. 50 mM S-(2-aminoethyl)-L-cysteine and 10 mM L-threonine, when compared to the wild form of the enzyme, which is contained in wild strains like for example ATCC13032, ATCC14067 and ATCC13869. The EC number for aspartokinase is EC 2.7.2.4. Descriptions of polynucleotides of *Corynebacterium glutamicum* encoding a feedback resistant aspartokinase polypeptide variant are for example given in U.S. Pat. Nos. 5,688,671, 6,844,176 and 6,893,848. A summarizing list can be found inter alia in WO2009141330. The symbol used in the art for a gene coding for an aspartokinase polypeptide is lysC. In case the gene codes for a feedback resistant polypeptide variant the art typically uses symbols like lysC$^{fbr}$ with fbr indicating feedback resistance.

Accordingly, said L-lysine excreting strains of the species *Corynebacterium glutamicum* used for the measures of the present invention preferably contain at least one copy of a polynucleotide coding for a feedback resistant aspartokinase polypeptide.

SEQ ID NO:5 shows the nucleotide sequence of the coding sequence of the aspartokinase polypeptide of strain ATCC13032 and SEQ ID NO:6 the amino acid sequence of the encoded polypeptide. It is known in the art (see U.S. Pat. No. 6,893,848) that exchange of the amino acid Thr at position 311 of SEQ ID NO:6 for Ile imparts the enzyme feedback resistance to inhibition by mixtures of L-lysine and L-threonine. Accordingly, it is preferred that the amino acid sequence of said feedback resistant aspartokinase polypeptide comprises the amino acid sequence of SEQ ID NO:6 containing isoleucine at position 311 instead of threonine.

Said amino exchange can be achieved by exchanging the nucleobase cytosine (c) at position 932 of SEQ ID NO:5 to give thymine (t). The acc codon for threonine is thus altered to the atc codon for isoleucine.

The exchange of the gtg start codon of the coding sequence for the aspartokinase polypeptide for atg enhances expression of the polypeptide (c.f. e.g. EP2796555 A2). Accordingly, it is preferred that the sequence coding for a feedback resistant aspartokinase polypeptide begins with an atg start codon.

L-lysine excreting strains of the species *Corynebacterium glutamicum* are widely known in the art and can be modified as described in the present invention. For example, U.S. Pat. No. 7,338,790 B2 describes strain DM1797. It is deposited according to the Budapest treaty at the DSMZ under accession number DSM16833. DM1797 is an aminoethylcystein resistant mutant of strain ATCC13032 obtained after N'-methyl-N-nitro-nitrosoguanidine mutagenesis. For example, Blombach et al. (Applied and Environmental Microbiology 75(2), 419-427, 2009) describe strain DM1933, which is deposited under accession DSM25442 according to the Budapest treaty. Strain DM1933 was obtained from ATCC13032 by several steps of strain development. Furthermore L-lysine excreting *Corynebacterium glutamicum* strain DM2031, deposited according to the Budapest Treaty as DSM32514 may be used. Strain DM2031 is a further developed derivative of DM1933 having enhanced L-lysine excretion ability. Other L-lysine excreting *Corynebacterium glutamicum* strains are e.g. described in WO2008033001 and EP0841395.

The term DSM denotes the depository Deutsche Sammlung für Mikroorganismen und Zellkulturen located in Braunschweig, Germany. The term ATCC denotes the depository American Type Culture Collection located in Manassas, Va., US.

Teachings and information concerning the handling of and experimental work with polynucleotides may be found inter alia in the handbook of J. Sambrook et al. (Molecular Cloning, A Laboratory Manual, Cold Spring Harbor Laboratory Press, 1989), the textbook of C. R. Newton and A. Graham (PCR, Spektrum Akademischer Verlag, 1994) and the handbook of D. Rickwood and B. D. Hames (Gel electrophoresis of nucleic acids, a practical approach, IRL Press, 1982).

During the work for the present invention it was found that modifying L-lysine excreting bacteria of the species *Corynebacterium glutamicum* by exchanging the amino acid serine at position 225 of the encoded amino acid sequence of the polypeptide shown in SEQ ID NO:2 for a different proteinogenic, preferably cysteine, increased their ability to excrete L-lysine as compared to the unmodified bacterium.

A mutant bacterium according to the invention can be obtained by classical in vivo mutagenesis executed with cell populations of strains of *Corynebacterium glutamicum* using mutagenic substances, e.g. N-methyl-N'-nitro-N-nitrosoguanidine, or ultra violet light. The nucleotide sequence comprising the site of mutagenesis within the gene can be amplified by PCR using primers selected from SEQ ID NO:1 or SEQ ID NO:3. By sequencing the PCR product the desired mutants are identified. Details concerning this approach can be found inter alia in U.S. Pat. No. 7,754,446.

A further method of mutagenesis is the CRISPR-Cpf1 assisted genome editing described by Jiang et al. (Nature Communications, 2017 May 8, 15179. DOI:10.1038/ncomms15179) or the CRISPR-Cas9 assisted genome editing described by Cho et al. (Metabolic Engineering, 2017 July; 42:157-167. doi: 10.1016/j.ymben.2017.06.010.), Peng et al. (Microbial Cell Factories, 2017 Nov. 14:16(1): 201. doi: 10.1186/s112934-017-0814-6.) and Liu et al. (Microbial Cell Factories, 2017 Nov. 16; 16(1):205. doi: 10.1186/s12934-017-0815-5.).

Another common method of mutating genes of *Corynebacterium glutamicum* is the method of gene replacement described by Schwarzer and Pühler (Bio/Technology 9, 84-87 (1991)) and further elaborated by Schafer et al. (Gene 145, 69-73 (1994)).

Peters-Wendisch et al. (Microbiology 144, 915-927 (1998)) used the gene replacement method to inactivate the pyc gene of *Corynebacterium glutamicum* encoding pyruvate carboxylase In U.S. Pat. No. 7,585,650 the method was applied to the zwf gene to realize an amino acid exchange at position 321 of the amino acid sequence of the Zwf sub-unit of the glucose 6-phosphate dehydrogenase. In U.S. Pat. No. 7,754,446 the method was applied to the rel gene to realize an amino acid exchange at position 38 of the amino acid sequence of the GTP-pyrophosphate kinase polypeptide.

In the gene replacement method, a mutation, for example, a deletion, insertion or substitution of at least one nucleobase, is provided by an isolated polynucleotide comprising the nucleotide sequence of the gene in question or a part thereof containing the mutation.

In the context of the present invention the nucleotide sequence of the gene in question is the gene identified by locus_tag NCgl0292.

In the context of the present invention the mutation is a substitution of at least one nucleobase located in the codon specifying the amino acid serine at position 225 of the encoded amino acid sequence (see SEQ ID NO:1) of the NCgl0292 polypeptide.

As a consequence of said mutation the codon specifies a proteinogenic amino acid different from serine, preferably cysteine. The codons specifying cysteine are tgt or tgc. The codon tgc is preferred.

The codon for the amino acid at position 225 of the amino acid sequence has the position from 1000 to 1002 in SEQ ID NO:1 or SEQ ID NO:3. The nucleotide sequence from position 1000 to 1002, in particular the nucleotide at position 1001, may also be referred to as site of mutation.

The mutated nucleotide sequence of the gene in question or a part thereof containing the mutation comprises i) a nucleotide sequence at the 5'-end of the site of mutation, which is also referred to as 5'-flanking sequence or upstream sequence in the art, ii) a nucleotide sequence at the 3'-end of the site of mutation, which is also referred to as 3'-flanking sequence or downstream sequence in the art, and iii) the nucleotide sequence of the site of mutation between i) and ii).

Said 5'-flanking sequence and 3'-flanking sequence required for homologous recombination typically have a length of at least 200 bp, at least 400 bp, at least 600 bp or at least 800 bp. The maximum length typically is 1000 bp, 1500 bp or 2000 bp.

An example of a polynucleotide comprising a mutated nucleotide sequence in the context of the present invention is shown in SEQ ID NO:7. The nucleotide sequence of SEQ ID NO:7 from positions 24 to 1511 corresponds to SEQ ID NO:3 from positions 261 to 1748. The polynucleotide shown in SEQ ID NO:7 contains at its 5'- and 3'-end recognition sites for restriction endonucleases useful for cloning purposes. SEQ ID NO:7 contains the coding sequence of a variant of the NCgl0292 polypeptide described in this invention. The 5'-flanking sequence consists of the nucleotide sequence from positions 24 to 763 of SEQ ID NO:7. The 3'-flanking sequence consists of the nucleotide sequence from positions 765 to 1511 of SEQ ID NO:7. The site of mutation is at position 764 of SEQ ID NO:7.

The mutated nucleotide sequence provided is cloned into a plasmid vector, e.g. pK18mobsacB described by Schafer et al. (Gene 145, 69-73 (1994)) that is not capable of autonomous replication in *Corynebacterium glutamicum*. Said plasmid vector comprising said mutated nucleotide sequence is subsequently transferred into the desired strain of *Corynebacterium glutamicum* by transformation or conjugation. After two events of homologous recombination comprising a recombination event within the 5'-flanking sequence provided by the plasmid vector with the homologous sequence of the *Corynebacterium glutamicum* chromosome and a recombination event within the 3'-flanking sequence provided by the plasmid vector with the homologous sequence of the *Corynebacterium glutamicum* chromosome, one effecting integration and one effecting excision of said plasmid vector, the mutation is incorporated in the *Corynebacterium glutamicum* chromosome. Thus, the nucleotide sequence of the gene in question contained in the chromosome of said desired strain is replaced by the mutated nucleotide sequence. The presence of the mutation in the desired strain is then confirmed e.g. by analysis of the nucleotide sequence or real-time PCR using FRET as described above.

An event of homologous recombination may also be referred to as crossing over.

The invention further provides a fermentative process for producing L-lysine using the *Corynebacterium glutamicum* of the present invention.

In a fermentative process according to the invention, a *Corynebacterium glutamicum* modified in accordance with the present invention and having the ability to excrete L-lysine is cultivated in a suitable medium under suitable conditions. Due to said ability to excrete said L-lysine the concentration of the L-lysine increases and accumulates in the medium during the fermentative process and the L-lysine is thus produced.

The fermentative process may be discontinuous process like a batch process or a fed batch process or a continuous process. A summary concerning the general nature of fermentation processes is available in the textbook by H. Chmiel (Bioprozesstechnik, Spektrum Akademischer Verlag, 2011), in the textbook of C. Ratledge and B. Kristiansen (Basic Biotechnology, Cambridge University Press, 2006) or in the textbook of V. C. Hass and R. Pörtner (Praxis der Bioprozesstechnik Spektrum Akademischer Verlag, 2011).

A suitable medium used for the production of L-lysine by a fermentative process contains a carbon source, a nitrogen source, a phosphorus source, inorganic ions and other organic compounds as required.

Suitable carbon sources include glucose, fructose, sucrose as well as the corresponding raw materials like starch hydrolysate, molasses or high fructose corn syrup.

As nitrogen source organic nitrogen-containing compounds such as peptones, meat extract, soy bean hydrolysates or urea, or inorganic compounds such as ammonium sulphate, ammonium chloride, ammonium phosphate, ammonium carbonate, ammonium nitrate, ammonium gas or aqueous ammonia can be used.

As phosphorus source, phosphoric acid, potassium dihydrogen phosphate or dipotassium hydrogen phosphate or the corresponding sodium-containing salts can be used.

Inorganic ions like potassium, sodium, magnesium, calcium, iron and further trace elements etc. are supplied as salts of sulfuric acid, phosphoric acid or hydrochloric acid.

Other organic compounds mean essential growth factors like vitamins e. g. thiamine or biotin or L-amino acids e. g. L-homoserine.

The media components may be added to the culture in form of a single batch or be fed in during the cultivation in a suitable manner.

During the fermentative process, the pH of the culture can be controlled by employing basic compounds such as sodium hydroxide, potassium hydroxide, ammonia or aqueous ammonia, or acidic compounds such as phosphoric acid or sulphuric acid in a suitable manner. The pH is generally adjusted to a value of from 6.0 to 8.5, preferably 6.5 to 8.0. To control foaming, it is possible to employ antifoam agents such as, for example, fatty acid polyglycol esters. To maintain the stability of plasmids, it is possible to add to the medium suitable selective substances such as, for example, antibiotics. The fermentative process is preferably carried out under aerobic conditions. In order to maintain these conditions, oxygen or oxygen-containing gas mixtures such as, for example air are introduced into the culture. The fermentative process is carried out, where appropriate, at elevated pressure, for example at an elevated pressure of 0.03 to 0.2 MPa. The temperature of the culture is normally from 25° C. to 40° C., preferably from 30° C. to 37° C. In a discontinuous process, the cultivation is continued until an amount of the L-lysine sufficient for being recovered has been formed. The cultivation is then completed. This aim is normally achieved within 10 hours to 160 hours. In continuous processes, longer cultivation times are possible.

Thus, the fermentative process results in a fermentation broth which contains the desired L-lysine.

Accordingly, a method for the fermentative production of L-lysine is provided comprising the steps of
a) cultivating a *Corynebacterium glutamicum* of the present invention in a suitable medium under suitable conditions, and
b) accumulating said L-lysine in the medium to produce an L-lysine containing fermentation broth.

A product containing the L-lysine is then recovered in liquid or solid from the fermentation broth.

A "fermentation broth" means a medium in which a *Corynebacterium glutamicum* of the invention has been cultivated for a certain time and under certain conditions.

When the fermentative process is completed, the resulting fermentation broth accordingly comprises: the biomass (cell mass) of the *Corynebacterium glutamicum* of the invention, said biomass having been produced due to propagation of the cells of said *Corynebacterium glutamicum*, the desired L-lysine accumulated during the fermentative process, the organic by-products accumulated during the fermentative process, and the components of the medium employed which have not been consumed in the fermentative process.

The organic by-products include compounds which may be formed by the *Corynebacterium glutamicum* during the fermentative process according to the present invention in addition to production of the L-lysine.

The fermentation broth is removed from the culture vessel or fermentation tank, collected where appropriate, and used for providing a product containing the L-lysine, in liquid or solid form. The expression "recovering the L-lysine-containing product" is also used for this. In the simplest case, the L-lysine-containing fermentation broth itself, which has been removed from the fermentation tank, constitutes the recovered product.

The fermentation broth can subsequently be subjected to extracting or substantially eliminating water from said fermentation broth.

Removal of the biomass can be achieved inter alia by centrifugation, filtration or decantation or a combination thereof.

Manufacturing of an L-lysine product may also comprise a purification step, preferably selected from the group consisting ion exchange chromatography, treatment with activated carbon or crystallization.

Thus e. g. a product containing L-lysine×HCl, preferably containing >80% L-lysine×HCl, particularly preferred >90% L-lysine×HCl or >95% L-lysine×HCl can be obtained.

Analysis of L-lysine to determine its concentration at one or more time(s) during the fermentation can take place by separating the L-lysine by means of ion exchange chromatography, preferably cation exchange chromatography, with subsequent post-column derivatization using ninhydrin, as described in Spackman et al. (Analytical Chemistry 30: 1190-1206 (1958)). It is also possible to employ ortho-phthalaldehyde rather than ninhydrin for post-column derivatization. An overview article on ion exchange chromatography can be found in Pickering (LC.GC (Magazine of Chromatographic Science 7(6):484-487 (1989)). It is likewise possible to carry out a pre-column derivatization, for example using ortho-phthalaldehyde or phenyl isothiocyanate, and to fractionate the resulting amino acid derivates by reversed-phase chromatography (RP), preferably in the form of high-performance liquid chromatography (HPLC). A method of this type is described, for example, in Lindroth et al. (Analytical Chemistry 51:1167-1174 (1979)). Detection is carried out photometrically (absorption, fluorescence). A review regarding amino acid analysis can be found inter alia in the textbook "Bioanalytik" by Lottspeich and Zorbas (Spektrum Akademischer Verlag, Heidelberg. Germany 1998).

Experimental Section

A) Materials and Methods

The molecular biology kits, primers and chemicals used and some details of the methods applied are briefly described herewith.

1. Antibiotics and Chemicals a. Kanamycin: Kanamycin solution from *Streptomyces kanamyceticus* from Sigma Aldrich (St. Louis, USA, Cat. no. K0254).

b. Nalidixic acid: Nalidixic acid sodium salt from Sigma Aldrich (St. Louis, USA, Cat. no. N4382).

c. If not stated otherwise, all chemicals were purchased analytically pure from Merck (Darmstadt, Germany), Sigma Aldrich (St. Louis, USA) or Carl-Roth (Karlsruhe, Germany).

2. Cultivation

If not stated otherwise, all cultivation/incubation procedures were performed as follows herewith:

a. LB broth (MILLER) from Merck (Darmstadt, Germany; Cat. no. 110285) was used to cultivate *E. coli* strains in liquid medium. The liquid cultures (10 ml liquid medium per 100 ml Erlenmeyer flask with 3 baffles) were incubated in the Infors HT Multitron standard incubator shaker from Infors GmbH (Einsbach, Germany) at 37° C. and 200 rpm.

b. LB agar (MILLER) from Merck (Darmstadt, Germany Cat. no. 110283) was used for cultivation of *E. coli* strains on agar plates. The agar plates were incubated at 37° C. in an INCU-Line® mini incubator from VWR (Radnor, USA).

c. Brain heart infusion broth (BHI) from Merck (Darmstadt, Germany; Cat. no. 110493) was used to cultivate *C. glutamicum* strains in liquid medium. The liquid cultures (10 ml liquid medium per 100 ml Erlenmeyer flask with 3 baffles) were incubated in the Infors HT Multitron standard incubator shaker from Infors GmbH (Einsbach, Germany) at 33° C. and 200 rpm.

d. Brain heart agar (BHI-agar) from Merck (Darmstadt, Germany; Cat. no. 113825) was used for cultivation of *C. glutamicum* strains on agar plates. The agar plates were incubated at 33° C. in an incubator from Heraeus Instruments with Kelvitron® temperature controller (Hanau, Germany).

3. Determining Optical Density a. The optical density of bacterial suspensions in shake flask cultures was determined at 600 nm (OD600) using the BioPhotometer from Eppendorf AG (Hamburg, Germany).

b. The optical density of bacterial suspensions produced in the Wouter Duetz (WDS) micro fermentation system (24-Well Plates) was determined at 660 nm (OD660) with the GENios™ plate reader from Tecan Group AG (Männedorf, Switzerland).

4. Centrifugation a. Benchtop Centrifuge for Reaction Tubes with a Volume Up to 2 ml

Bacterial suspensions with a maximum volume of 2 ml were caused to sediment using 1 ml or 2 ml reaction tubes (e.g. Eppendorf Tubes® 3810X) using an Eppendorf 5417 R centrifuge (5 min. at 13.000 rpm).

b. Benchtop Centrifuge for Tubes with a Volume Up to 50 ml

Bacterial suspensions with a maximum volume of 50 ml were caused to sediment using 15 ml or 50 ml centrifuge tubes (e.g. Falcon™ 50 ml Conical Centrifuge Tubes) using an Eppendorf 5810 R centrifuge for 10 min. at 4.000 rpm.

5. Detection of Mutations Using FRET

The presence of a given mutation, e.g. a nucleobase exchange, was detected by real-time PCR in combination with FRET hybridization probes. The term FRET is the abbreviation for fluorescence resonance energy transfer. As real-time PCR instrument a Lightcycler from Roche Diagnostics® was used (see below).

This method was e. g. used by M. J. Lay and C. T. Wittwer (Clinical Chemistry 42 (12), 2262-2267 (1997)) for the genotyping of factor V Leiden. Cyril DS Mamotte (The Clinical Biochemist Reviews 27, 63-75 (2006) reviews the genotyping of single nucleotide substitutions using this method. Summaries concerning this method may be found in the textbooks Lewin's Genes XII by Jocelyn E. Krebs, Elliott S. Goldstein and Stephan T. Kilpatrick (Jones and Bartlett Publishers, US, 2018), Molecular Diagnostics, 12 Tests that changed everything by W. Edward Highsmith (Humana Press, Springer, New York, 2014) or elsewhere in the art.

The FRET hybridization donor probe was labelled with the fluorescent dye fluorescein and the acceptor probe with the fluorescent dye LC-Red640. In essence the detection method comprised three steps: colony PCR, probe hybridization and subsequent melting curve analysis. The method is simply referred to as real-time PCR herewith.

a. Primers and Probes

The oligonucleotides used were synthesized by eurofins genomics GmbH (Ebersberg, Germany).

b. Template

As PCR template the total DNA contained in a colony was used. It was prepared by taking cell material with a toothpick from a colony on an agar plate and placing the cell material directly into the PCR reaction tube. The cell material was heated for 10 sec. with 800 W in a microwave oven type Mikrowave & Grill from SEVERIN Elektrogerate GmbH (Sundern, Germany) and then the PCR reagents were added to the template in the PCR reaction tube.

b. Reaction Mix

The Type-It® Fast SNP probe PCR Kit (Type-it Kit) from Qiagen (Hilden, Germany, Cat. No. 206045) was used for real-time detection of the mutations. Therefore 2.5 µl of the Qiagen Fast SNP Puffer (2×) was mixed with 0.5 µl of each of the LC-PCR-Primers [10 µM] and 0.5 µl of each of the 1:500 diluted acceptor and donor probe [100 pmol/µl] to get the mastermix for the real-time PCR.

TABLE 1

Thermocycling conditions for PCR with the LightCycler® (step 1-3) and melting curve analysis (step 4-6).
PCR-program

| Step | Time [sec.] | T [° C.] | Description |
|---|---|---|---|
| 1 | 15 | 95 | Denaturation step (and Activation of HotStarTaq ™ DNA polymerase) |
| 2 | 05 | 55 | Annealing step |
| 3 | 30 | 72 | Elongation step |
| | | | Repeat step 1 to 3: 50 x |
| 4 | 10 | 95 | Denaturation step |
| 5 | 30 | 40 | Probe hybridization |
| 6 | | 40-80 | Melting curve analysis |
| 7 | | 80-40 | Cooling | c. PCR Cycler

The reactions were carried out in a LightCycler® 2.0 Instrument and analyzed with LightCycler® Software 4.1 of Roche Diagnostics (Rotkreuz, Switzerland).

6. Chemical Transformation of E. coli

E. coli K-12 strain S17-1 was used as donor for conjugational transfer of plasmids based on pK18mobsacB from E. coli to C. glutamicum. Strain S17-1 is described by Simon, R. et al. (Bio/Technology 1, 784-794, 1983). It is available from the American Type Culture Collection under the access number ATCC47055.

Chemically competent E. coli S17-1 cells were made as follows: A preculture of 10 ml LB medium (10 ml liquid medium per 100 ml Erlenmeyer flask with 3 baffles) was inoculated with 100 µl bacterial suspension of strain S17-1 and the culture was incubated overnight for about 18 h at 37° C. and 250 rpm. The main culture (70 ml LB contained in a 250 ml Erlenmeyer flask with 3 baffles) was inoculated with 300 µl of the preculture and incubated up to an OD600 of 0.5-0.8 at 37° C. The culture was centrifuged for 6 min. at 4° C. and 4000 rpm and the supernatant was discarded. The cell pellet was resuspended in 20 ml sterile, ice-cold 50 mM $CaCl_2$) solution and incubated on ice for 30 min. After another centrifugation step, the pellet was resuspended in 5 ml ice-cold 50 mM $CaCl_2$) solution and the suspension incubated on ice for 30 min. The cell suspension was then adjusted to a final concentration of 20% glycerol (v/v) with 85% (v/v) sterile ice-cold glycerol. The suspension was divided into 50 µl aliquots and stored at −80° C.

To transform S17-1 cells, the protocol according to Tang et al. (Nucleic Acids Res. 22(14), 2857-2858, 1994) with a heat shock of 45 sec. was used.

7. Conjugation of C. glutamicum

The pK18mobsacB plasmid system described by Schafer et al. (Gene 145, 69-73, 1994) was used to integrate desired DNA fragments into the chromosome of C. glutamicum. A modified conjugation method of Schafer et al. (Journal of Bacteriology 172, 1663-1666, 1990) was used to transfer the respective plasmid into the desired C. glutamicum recipient strain.

Liquid cultures of the C. glutamicum strains were carried out in BHI medium at 33° C. The heat shock was carried out at 48.5° C. for 9 min. Transconjugants were selected by plating the conjugation batch on EM8 agar (Table 2), which was supplemented with 25 mg/l kanamycin and 50 mg/l nalidixic acid. The EM8 agar plates were incubated for 72 h at 33° C.

TABLE 2

Composition of the EM8 agar

| Components | Concentration (g/l) |
|---|---|
| Glucose (sterile-filtered) | 23 |
| CSL (corn steep liquor; Roquette; solid content 48 ± 2% w/w) | 30 |
| Peptone from soymeal (Merck, Germany) | 40 |
| $(NH_4)_2SO_4$ | 8 |
| Urea | 3 |
| $KH_2PO_4$ | 4 |
| $MgSO_4 \cdot 7\ H_2O$ | 0.5 |
| $FeSO_4 \cdot 7\ H_2O$ | 0.01 |
| $CuSO_4 \cdot 5\ H_2O$ | 0.001 |
| $ZnSO_4 \cdot 7\ H_2O$ | 0.01 |
| Calcium pantothenate, D(+) | 0.01 |
| Thiamine | 0.001 |
| Inositol | 0.1 |
| Nicotinic acid | 0.001 |
| Biotin (sterile-filtered) | 0.005 |
| $CaCO_3$ (autoclaved separately) | 1.6 |
| Agar-Agar (Merck, Germany) | 14 |

Sterile toothpicks were used to transfer the transconjugants onto BHI agar, which was supplemented with 25 mg/l kanamycin and 50 mg/l nalidixic acid. The agar plates were incubated for 20 h at 33° C. The cultures of the respective transconjugants produced in this manner were then propagated further for 24 h at 33° C. in 10 ml BHI medium contained in 100 ml Erlenmeyer flasks with 3 baffles. An aliquot was taken from the liquid culture suitably diluted and plated (typically 100 to 200 μl) on BHI agar which was supplemented with 10% saccharose. The agar plates were incubated for 48 h at 33° C. The colonies growing on the saccharose containing agar plates were then examined for the phenotype kanamycin sensitivity. To do so a toothpick was used to remove cell material from the colony and to transfer it onto BHI agar containing 25 mg/l kanamycin and onto BHI agar containing 10% saccharose. The agar plates were incubated for 60 h at 33° C. Clones that proved to be sensitive to kanamycin and resistant to saccharose were examined for integration of the desired DNA fragment by means of real-time PCR 8. Glycerol Stocks of *E. coli* and *C. glutamicum* Strains For long time storage of *E. coli*- and *C. glutamicum* strains glycerol stocks were prepared. Selected *E. coli* clones were cultivated in 10 ml LB medium supplemented with 2 g/l glucose. Selected *C. glutamicum* clones were cultivated in two-fold concentrated BHI medium supplemented with 2 g/l glucose. Cultures of plasmid containing *E. coli* strains were supplemented with 50 mg/l kanamycin. Cultures of plasmid containing *C. glutamicum* strains were supplemented with 25 mg/l kanamycin. The medium was contained in 100 ml Erlenmeyer flasks with 3 baffles. It was inoculated with a loop of cells taken from a colony and the culture incubated for about 18 h at 37° C. and 200 rpm in the case of *E. coli* and 33° C. and 200 rpm in the case of *C. glutamicum*. After said incubation period 1.2 ml 85% (v/v) sterile glycerol were added to the culture. The obtained glycerol containing cell suspension was then aliquoted in 2 ml portions and stored at −80° C.

9. Cultivation System According to Wouter Duetz (WDS)

The millilitre-scale cultivation system according to Duetz (Trends Microbiol. 2007; 15(10):469-75) was used to investigate the performance of the *C. glutamicum* strains constructed. For this purpose, 24-deepwell microplates (24 well WDS plates) from EnzyScreen BV (Heemstede, Netherlands; Cat. no. CR1424), filled with 2.5 mL medium were used.

Precultures of the strains were done in 10 ml two-fold concentrated BHI medium. The medium was contained in a 100 ml Erlenmeyer flask with 3 baffles. It was inoculated with 100 μl of a glycerol stock culture and the culture incubated for 24 h at 33° C. and 200 rpm.

After said incubation period the optical densities OD600 of the precultures were determined.

The main cultures were done by inoculating the 2.5 ml medium containing wells of the 24 Well WDS-Plate with an aliquot of the preculture to give an optical density OD600 of 0.1.

As medium for the main culture CGXII medium described by Keilhauer et al. (J. Bacteriol. 1993 September; 175(17): 5595-5603) was used. For convenience the composition of the CGXII medium is shown in table 3.

TABLE 3

Composition of Keilhauer's CGXII medium.

| Components | Concentration (g/l) |
|---|---|
| MOPS (3-(N-Morpholino)propanesulfonic acid) | 42 |
| $(NH_4)_2SO_4$ | 20 |
| Urea | 5 |
| $KH_2PO_4$ | 1 |
| $K_2HPO_4$ | 1 |
| $MgSO_4 \cdot 7\ H_2O$ | 0.25 |
| $CaCl_2$ | 0.01 |
| $FeSO_4 \cdot 7\ H_2O$ | 0.01 |
| $MnSO_4\ H_2O$ | 0.01 |
| $ZnSO_4 \cdot 7\ H_2O$ | 0.001 |
| $CuSO_4 \cdot 5\ H_2O$ | 0.0002 |
| $NiCl_2\ 6\ H_2O$ | 0.00002 |
| Biotin (sterile-filtered) | 0.0002 |
| Protocatechuic acid (sterile-filtered) | 0.03 |
| Carbon source (sterile-filtered) | as needed |
| adjust the pH to 7 with NaOH | |

These main cultures were incubated for approximately 45 h at 33° C. and 300 rpm in an Infors HT Multitron standard incubator shaker from Infors GmbH (Bottmingen, Switzerland) until complete consumption of glucose.

The glucose concentration in the suspension was analyzed with the blood glucose-meter OneTouch Vita® from LifeScan (Johnson & Johnson Medical GmbH, Neuss, Germany). After cultivation the culture suspensions were transferred to a deep well microplate. A part of the culture suspension was suitably diluted to measure the OD600. Another part of the culture was centrifuged and the concentration of L-amino acids, in particular L-lysine, and residual glucose were analyzed in the supernatant.

10. Amino Acid Analyzer

The concentration of L-lysine and other L-amino acids in the culture supernatants was determined by ion exchange chromatography using a SYKAM S433 amino acid analyzer from SYKAM Vertriebs GmbH (Fürstenfeldbruck, Germany). As solid phase a column with spherical, polystyrene-based cation exchanger (Peek LCA N04/Na, dimension 150×4.6 mm) from SYKAM was used. Depending on the L-amino acid the separation takes place in an isocratic run using a mixture of buffers A and B for elution or by gradient elution using said buffers. As buffer A an aqueous solution containing in 20 l 263 g trisodium citrate, 120 g citric acid, 1100 ml methanol, 100 ml 37% HCl and 2 ml octanoic acid (final pH 3.5) was used. As buffer B an aqueous solution containing in 20 l 392 g trisodium citrate, 100 g boric acid and 2 ml octanoic acid (final pH 10.2) was used. The free amino acids were coloured with ninhydrin through post-column derivatization and detected photometrically at 570 nm.

11. Glucose Determination with Continuous Flow System (CFS)

A SANplus multi-channel continuous flow analyzer from SKALAR analytic GmbH (Erkelenz, Germany) was used to determine the concentration of glucose in the supernatant. Glucose was detected with a coupled-enzyme assay (Hexokinase/Glucose-6-Phosphate-Dehydrogenase) via NADH formation.

B) Experimental Results

Example 1

Sequence of the NCgl0292 Gene of C. glutamicum Strain DM1933

Strain DM1933 is an L-lysine producer described by Blombach et al. (Applied and Environmental Microbiology 75(2), 419-427, 2009). It is deposited according to the Budapest treaty at the DSMZ under accession number DSM25442. C. glutamicum DM1933 has the following characteristics (c.f. Blombach et al. Applied and Environmental Microbiology 75(2), 419-427, 2009; Page 420, Table 1): Δpck pyc(P458S) hom(V59A), 2 copies of lysC(T3111), 2 copies of asd, 2 copies of dapA, 2 copies of dapB, 2 copies of ddh, 2 copies of lysA, 2 copies of lysE (derived from wild type strain of C. glutamicum ATCC13032).

The nucleotide sequence of the chromosome of strain DM1933 was determined by Illumina whole-genome sequencing technology (Illumina Inc., San Diego, Calif. US). See e.g. Benjak et al. (2015) Whole-Genome Sequencing for Comparative Genomics and De Novo Genome Assembly. In: Parish T., Roberts D. (eds) Mycobacteria Protocols. Methods in Molecular Biology, Vol 1285. Humana Press, NY, US) and Bennet, S. (Pharmacogenomics 5(4), 433-438, 2004). It was found that the nucleotide sequence of the NCgl0292 coding sequence of strain DM1933 including the nucleotide sequence upstream and downstream thereof is identical to that of ATCC13032 shown in SEQ ID NO:1.

DM1933 contains in its chromosome a variant of the aspartokinase gene (lysC) encoding a feedback resistant aspartokinase polypeptide. Said feedback resistant aspartokinase polypeptide has the amino acid sequence of SEQ ID NO:6 of the sequence listing, wherein the amino acid threonine (Thr) at position 311 of the amino acid sequence is replaced by isoleucine (Ile). In U.S. Pat. No. 7,338,790 the abbreviation "lysC T311 I" is used to indicate said exchange. Blombach et al. use the abbreviation "lysC(T3111)".

Example 2

Construction of Plasmid pK18mobsacB_NCgl0292_S225C

Plasmid pK18mobsacB_NCgl0292_S225C was constructed to enable incorporation of the mutation causing the amino acid exchange S225C into the nucleotide sequence of the NCgl0292 coding sequence of strain DM1933. The plasmid is based on the mobilizable vector pK18mobsacB described by Schafer et al. (Gene 145, 69-73, 1994). For the construction of pK18mobsacB_NCgl0292_S225C the NCgl0292_S225C sequence according to SEQ ID NO:7 was synthesized and subcloned into pK18mobsacB by GeneArt (ThermoFisher Scientific (Waltham, USA)).

The assembly of the plasmid pK18mobsacB_NCgl0292_S225C was done by GeneArt (ThermoFisher Scientific (Waltham, USA)) as follows: the two polynucleotides i.e. the vector pK18mobsacB cut with SbfI and XmaI and the polynucleotide NCgl0292_S225C cut with SbfI plus XmaI were ligated and the ligation mixture used to transform E. coli. Plasmid DNA was then isolated from the transformant.

Example 3

Construction of Strain DM1933_NCgl0292_S225C

The plasmid pK18mobsacB_NCgl0292_S225C obtained in example 2 was used to incorporate the mutation leading to the amino acid exchange S225C (see nucleotide position 764 of SEQ ID No:7) into the chromosome of the L-lysine producer DM1933. Chemically competent cells of E. coli strain S17-1 were transformed with plasmid DNA of pK18mobsacB_NCgl0292_S225C. The modified conjugation method of Schafer et al. (Journal of Bacteriology 172, 1663-1666, 1990) as described in materials and methods was used for conjugal transfer into the strain DM1933 and for selection of transconjugant clones by virtue of their saccharose resistance and kanamycin sensitivity phenotype. Transconjugant clones were analyzed by real-time PCR using the Type-it Kit and the primers NCgl0292_fw and NCgl0292_rev for PCR amplification and NCgl0292_C as acceptor probe and NCgl0292_A as donor probe for melting curve analysis (table 4). Said primers and probes are also shown under SEQ ID NO's 9 to 12 of the sequence listing.

TABLE 4

List of primers and probes used for real-time PCR.

| name | sequence | SEQ ID NO: |
|---|---|---|
| NCgl0292_fw | CAACGAGGTAGCGGTTGGTG | 9 |
| NCgl0292_rev | TCCGCGGCCTAATTTCCCTC | 10 |
| NCgl0292_C[1] | ACAACACGTGCTCGTCCTAC | 11 |
| NCgl0292_A[2] | TTCGGAATCACCAGCGAAGCTCGACGTGAGATCGT | 12 |

[1]acceptor probe labelled with LC-Red640 at the 5'-end and phosphorylated at the 3'-end
[2]donor probe labelled with fluorescein at the 3'-end One of the transconjugant clones thus characterized was called DM1933_NCgl0292_S225C. A glycerol stock culture of the transconjugant clone was prepared and used as starting material for further investigations.

Thus, the NCgl0292 gene of strain DM1933 was mutated with the effect that the amino acid serine at position 225 of the amino acid sequence of the encoded NCgl0292 polypeptide was replaced by cysteine.

Example 4

L-Lysine Production by Strain DM1933_NCgl0292_S225C

Strains DM1933 (reference) and DM1933_NCgl0292_S225C obtained in example 3 were analyzed for their ability to produce L-lysine from glucose by batch cultivation using the cultivation system according to Wouter Duetz.

As medium CGXII containing 20 g/l glucose as carbon source was used. The cultures were incubated for 45 h until complete consumption of glucose as confirmed by glucose analysis using blood glucose-meter and the concentrations of L-lysine and the optical density OD660 were determined. The result of the experiment is presented in table 5.

TABLE 5

L-lysine production by strain DM1933_NCgl0292_S225C.

| strain | L-lysine[1] (g/l) | OD660 |
|---|---|---|
| DM1933 | 3.8 | 9.2 |
| DM1933_NCgl0292_S225C | 4.0 | 9.1 |

[1]as L-lysine x HCl

The experiment shows that L-lysine production was increased in strain DM1933_NCgl0292_S225C as compared to the parent strain DM1933.

The invention claimed is:

1. A bacterium of the species *Corynebacterium glutamicum*, comprising:
   an ability to excrete L-lysine, and
   a polynucleotide encoding a polypeptide comprising the amino acid sequence of SEQ ID NO: 2, except the serine at the position corresponding to position 225 of the amino acid sequence of SEQ ID NO: 2 is substituted with a different amino acid, and wherein the polynucleotide is contained in the chromosome of the bacterium.

2. The bacterium of claim 1, wherein the serine at the position corresponding to position 225 of the amino acid sequence of SEQ ID NO: 2 is substituted with cysteine.

3. The bacterium of claim 2, wherein the polynucleotide comprises the nucleotide sequence of nucleotides 328 to 1320 of SEQ ID NO: 1 with guanine at the position corresponding to position 1001 of SEQ ID NO: 1.

4. The bacterium of claim 2, wherein the polynucleotide comprises the nucleotide sequence of nucleotides 328 to 1323 of SEQ ID NO: 1 with guanine at the position corresponding to position 1001 of SEQ ID NO: 1.

5. The bacterium of claim 1, comprising at least one copy of a polynucleotide comprising a nucleotide sequence encoding a feedback resistant aspartokinase polypeptide, wherein the feedback resistant aspartokinase polypeptide comprises the amino acid sequence of SEQ ID NO: 6.

6. The bacterium of claim 1, comprising at least one copy of a polynucleotide comprising a nucleotide sequence encoding for a feedback resistant aspartokinase polypeptide comprising the amino acid sequence of SEQ ID NO: 6, except the threonine at the position corresponding to position 311 of the amino acid sequence of SEQ ID NO: 6 is substituted with isoleucine.

7. A method for fermentative production of L-lysine, comprising:
   a) cultivating the bacterium of claim 1 in a suitable medium under suitable conditions for the production of L-lysine, and
   b) accumulating L-lysine in the suitable medium to form an L-lysine containing fermentation broth.

8. The method of claim 7, further comprising:
   purifying L-lysine.

9. The method of claim 8, wherein L-lysine is purified by at least one process selected from the group consisting of treatment with activated carbon, ionic exchange, and crystallization.

\* \* \* \* \*

SEQUENCE LISTING

<160> NUMBER OF SEQ ID NOS: 12

<210> SEQ ID NO 1
<211> LENGTH: 2001
<212> TYPE: DNA
<213> ORGANISM: Corynebacterium glutamicum ATCC13032
<220> FEATURE:
<221> NAME/KEY: CDS
<222> LOCATION: (328)..(1320)
<223> OTHER INFORMATION: coding sequence of NCgl0292
<220> FEATURE:
<221> NAME/KEY: misc_feature
<222> LOCATION: (1000)..(1002)
<223> OTHER INFORMATION: tcc codon for serine
<220> FEATURE:
<221> NAME/KEY: misc_feature
<222> LOCATION: (1001)..(1001)
<223> OTHER INFORMATION: nucleobase cytosine
<220> FEATURE:
<221> NAME/KEY: misc_feature
<222> LOCATION: (1321)..(1323)
<223> OTHER INFORMATION: taa stop codon

<400> SEQUENCE: 1

```
tggcgtaatc gcactgtaca gctccttctt cttttcttc ttcgtcgcag cactgctgag      60
cgagtggatt aagccttggg cagcattcct catcgtgttc ctcttcatgc tggtcatcgc     120
cgcagctctc gcactgttcg gctggcgcaa ggtgaagaag atgggcgctc cgaagaacac     180
catccaatcg gtcaaccaac tgaagaacct ggtcccaggt caggcatccg agaagctgga     240
gaaggccaac aagcgtggcc tctacacctc cgcgtccttc acagccccg gcgccatcac      300 tggcgaccac taaaaaagga gacttcg atg gcc ttt ttt agc ttt tcg acg tct     354
                                 Met Ala Phe Phe Ser Phe Ser Thr Ser
                                  1               5 ccc ctc acc cgc ctc atc ccc ggc agc cgc tcc aaa gcc aca ggc gcc       402
Pro Leu Thr Arg Leu Ile Pro Gly Ser Arg Ser Lys Ala Thr Gly Ala
 10              15                  20                  25 aaa cgg cgc ctg agc agc aca atc gcg tcg att gaa cgc tcc ccc ggc       450
Lys Arg Arg Leu Ser Ser Thr Ile Ala Ser Ile Glu Arg Ser Pro Gly
             30                  35                  40 atc att gcc cta gac gga ccg ttc acc cac gat cac gtc tcc gta cgt       498
Ile Ile Ala Leu Asp Gly Pro Phe Thr His Asp His Val Ser Val Arg
         45                  50                  55 ggc att cgc ctc cat tta gca gag gca ggc tcc ccc acc aaa ccc ctg       546
Gly Ile Arg Leu His Leu Ala Glu Ala Gly Ser Pro Thr Lys Pro Leu
     60                  65                  70 gtt ctt ctg atc cac ggg gct ttc ggc ggt tgg tac gac tac cgc gaa       594
Val Leu Leu Ile His Gly Ala Phe Gly Gly Trp Tyr Asp Tyr Arg Glu
 75                  80                  85 gtc atc ggc cca ctc gca gat gcc ggc ttc cac gtc gcc gcc atc gat       642
Val Ile Gly Pro Leu Ala Asp Ala Gly Phe His Val Ala Ala Ile Asp
 90                  95                 100                 105
```

-continued

| | | |
|---|---|---|
| cta cgc ggc tac ggc atg tcc gac aaa ccc cca aca ggc tac gac ctc<br>Leu Arg Gly Tyr Gly Met Ser Asp Lys Pro Pro Thr Gly Tyr Asp Leu<br>          110                    115                   120 | 690 |

```
cta cgc ggc tac ggc atg tcc gac aaa ccc cca aca ggc tac gac ctc      690
Leu Arg Gly Tyr Gly Met Ser Asp Lys Pro Pro Thr Gly Tyr Asp Leu
            110                 115                 120 cgc cac gca gcc gga gaa ctc agc agc gtt atc gca gct ctc ggc cac      738
Arg His Ala Ala Gly Glu Leu Ser Ser Val Ile Ala Ala Leu Gly His
        125                 130                 135 gat gac gca ctt ctt gtc ggc tcc gac acc ggc gcc agc atc gcc tgg      786
Asp Asp Ala Leu Leu Val Gly Ser Asp Thr Gly Ala Ser Ile Ala Trp
    140                 145                 150 gct atc gct tcc atg tac ccc gaa cgg gtc cgc ggc cta att tcc ctc      834
Ala Ile Ala Ser Met Tyr Pro Glu Arg Val Arg Gly Leu Ile Ser Leu
155                 160                 165 ggc gcg atc cac ccc ctt gac atg cga cgc gcc atc cga cga aaa ccc      882
Gly Ala Ile His Pro Leu Asp Met Arg Arg Ala Ile Arg Arg Lys Pro
170                 175                 180                 185 cac cta cac gtc tct gac ctc agc cga ctt gct cct ttt cgg ttg ccc      930
His Leu His Val Ser Asp Leu Ser Arg Leu Ala Pro Phe Arg Leu Pro
                190                 195                 200 tca ttc ctg cat aac ctc ttc cac ttc gga atc acc agc gaa gct cga      978
Ser Phe Leu His Asn Leu Phe His Phe Gly Ile Thr Ser Glu Ala Arg
            205                 210                 215 cgt gag atc gtc aac aac acg tcc tcg tcc tac cag cgc agc aac gca     1026
Arg Glu Ile Val Asn Asn Thr Ser Ser Ser Tyr Gln Arg Ser Asn Ala
        220                 225                 230 ttc aca gag aca gtg ctc ctc cgc aaa aaa gca cta tcg atc gac cac     1074
Phe Thr Glu Thr Val Leu Leu Arg Lys Lys Ala Leu Ser Ile Asp His
    235                 240                 245 acc atc acc ccg atc atc cgc acc aac cgc tac ctc gtt ggg tcg atc     1122
Thr Ile Thr Pro Ile Ile Arg Thr Asn Arg Tyr Leu Val Gly Ser Ile
250                 255                 260                 265 ccc agc aaa aca gtc tcc gca ccg gtg tgg ctg ctc aga acc aac act     1170
Pro Ser Lys Thr Val Ser Ala Pro Val Trp Leu Leu Arg Thr Asn Thr
                270                 275                 280 cga cgc tgg gaa cat cta gcc aat act gcg cgc act cga acg aca ggg     1218
Arg Arg Trp Glu His Leu Ala Asn Thr Ala Arg Thr Arg Thr Thr Gly
            285                 290                 295 cca ttc acc acc atc gcg atc ccc ggc ggc tac gaa ctc ccc tac ctc     1266
Pro Phe Thr Thr Ile Ala Ile Pro Gly Gly Tyr Glu Leu Pro Tyr Leu
        300                 305                 310 gag aac cct tcc gaa ttt gca gca acc atc gca gag ttc gcg cgc acc     1314
Glu Asn Pro Ser Glu Phe Ala Ala Thr Ile Ala Glu Phe Ala Arg Thr
    315                 320                 325 acg ttt taagcactgt ggctgaggcg ctgctgctca tttggcgtca gaaggtcgca     1370
Thr Phe
330 tgatttggc gtgaattagt ggttttccc tggttttacc ccggcgcatt gaccggacca     1430
gacaggcgtg acaagaatca agattttcgc caggttttgt cacgtgtgtc tggtttgagc  1490
gactcgaaac caaacaggcg tgccaaaact tagatgtttt agcaattttt gtcacgtgtg  1550
tctggtttca tctagttcga ccgcaaacct cacggatttc ccctagtca ctcaaaaacc   1610 aaaactccct atatgcccct ctaagcgctt gggattcccc gacccatacc aatagacacc  1670
tctcctattc caggccctta aaacgccaca caggattggt cgtatctatc tcggattggg  1730
cgattcactg ccaagaccaa accacactgc ccacgcaacg gaaaaaccgc aatcgtgggc  1790
atctgtgacc ggttccgagc ccccaaaacc aaaccacact gcccacgcaa cggaaaaacc  1850
gcaatcgtgg gcatccctgt ctggtcctag ctcccgacga ctaagaaacc gcgcactgca  1910
```

```
tcgtatcgac aggctgagtc agcgcggtga tgtcgccgat ccgctcctgt acctcttcgg      1970
cagtgagaac gtaaccggta tcggagccgt c                                    2001
```

<210> SEQ ID NO 2
<211> LENGTH: 331
<212> TYPE: PRT
<213> ORGANISM: Corynebacterium glutamicum ATCC13032

<400> SEQUENCE: 2

```
Met Ala Phe Phe Ser Phe Ser Thr Ser Pro Leu Thr Arg Leu Ile Pro
1               5                   10                  15

Gly Ser Arg Ser Lys Ala Thr Gly Ala Lys Arg Arg Leu Ser Ser Thr
            20                  25                  30

Ile Ala Ser Ile Glu Arg Ser Pro Gly Ile Ile Ala Leu Asp Gly Pro
        35                  40                  45

Phe Thr His Asp His Val Ser Val Arg Gly Ile Arg Leu His Leu Ala
    50                  55                  60

Glu Ala Gly Ser Pro Thr Lys Pro Leu Val Leu Ile His Gly Ala
65                  70                  75                  80

Phe Gly Gly Trp Tyr Asp Tyr Arg Glu Val Ile Gly Pro Leu Ala Asp
                85                  90                  95

Ala Gly Phe His Val Ala Ala Ile Asp Leu Arg Gly Tyr Gly Met Ser
            100                 105                 110

Asp Lys Pro Pro Thr Gly Tyr Asp Leu Arg His Ala Ala Gly Glu Leu
        115                 120                 125

Ser Ser Val Ile Ala Ala Leu Gly His Asp Asp Ala Leu Leu Val Gly
    130                 135                 140

Ser Asp Thr Gly Ala Ser Ile Ala Trp Ala Ile Ala Ser Met Tyr Pro
145                 150                 155                 160

Glu Arg Val Arg Gly Leu Ile Ser Leu Gly Ala Ile His Pro Leu Asp
                165                 170                 175

Met Arg Arg Ala Ile Arg Arg Lys Pro His Leu His Val Ser Asp Leu
            180                 185                 190

Ser Arg Leu Ala Pro Phe Arg Leu Pro Ser Phe Leu His Asn Leu Phe
        195                 200                 205

His Phe Gly Ile Thr Ser Glu Ala Arg Arg Glu Ile Val Asn Asn Thr
    210                 215                 220

Ser Ser Ser Tyr Gln Arg Ser Asn Ala Phe Thr Glu Thr Val Leu Leu
225                 230                 235                 240

Arg Lys Lys Ala Leu Ser Ile Asp His Thr Ile Thr Pro Ile Ile Arg
                245                 250                 255

Thr Asn Arg Tyr Leu Val Gly Ser Ile Pro Ser Lys Thr Val Ser Ala
            260                 265                 270

Pro Val Trp Leu Leu Arg Thr Asn Thr Arg Arg Trp Glu His Leu Ala
        275                 280                 285

Asn Thr Ala Arg Thr Arg Thr Gly Pro Phe Thr Thr Ile Ala Ile
    290                 295                 300

Pro Gly Gly Tyr Glu Leu Pro Tyr Leu Glu Asn Pro Ser Glu Phe Ala
305                 310                 315                 320

Ala Thr Ile Ala Glu Phe Ala Arg Thr Thr Phe
                325                 330
```

<210> SEQ ID NO 3
<211> LENGTH: 2001
<212> TYPE: DNA

```
<213> ORGANISM: Corynebacterium glutamicum
<220> FEATURE:
<221> NAME/KEY: CDS
<222> LOCATION: (328)..(1320)
<223> OTHER INFORMATION: coding sequence of a variant of NCgl0292
<220> FEATURE:
<221> NAME/KEY: misc_feature
<222> LOCATION: (1000)..(1002)
<223> OTHER INFORMATION: tgc codon for cysteine
<220> FEATURE:
<221> NAME/KEY: misc_feature
<222> LOCATION: (1001)..(1001)
<223> OTHER INFORMATION: nucleobase guanine
<220> FEATURE:
<221> NAME/KEY: misc_feature
<222> LOCATION: (1321)..(1323)
<223> OTHER INFORMATION: taa stop codon

<400> SEQUENCE: 3
```

| | | |
|---|---|---|
| tggcgtaatc gcactgtaca gctccttctt ctttttcttc ttcgtcgcag cactgctgag | 60 |
| cgagtggatt aagccttggg cagcattcct catcgtgttc ctcttcatgc tggtcatcgc | 120 |
| cgcagctctc gcactgttcg gctggcgcaa ggtgaagaag atgggcgctc gaagaacac | 180 |
| catccaatcg gtcaaccaac tgaagaacct ggtcccaggt caggcatccg agaagctgga | 240 |
| gaaggccaac aagcgtggcc tctacacctc cgcgtccttc cacagcccg gcgccatcac | 300 |

| | |
|---|---|
| tggcgaccac taaaaaagga gacttcg atg gcc ttt ttt agc ttt tcg acg tct | 354 |
|                                               Met Ala Phe Phe Ser Phe Ser Thr Ser | |
|                                             1               5 | |
| ccc ctc acc cgc ctc atc ccc ggc agc cgc tcc aaa gcc aca ggc gcc | 402 |
| Pro Leu Thr Arg Leu Ile Pro Gly Ser Arg Ser Lys Ala Thr Gly Ala | |
| 10              15              20              25 | |
| aaa cgg cgc ctg agc agc aca atc gcg tcg att gaa cgc tcc ccc ggc | 450 |
| Lys Arg Arg Leu Ser Ser Thr Ile Ala Ser Ile Glu Arg Ser Pro Gly | |
|                30              35              40 | |
| atc att gcc cta gac gga ccg ttc acc cac gat cac gtc tcc gta cgt | 498 |
| Ile Ile Ala Leu Asp Gly Pro Phe Thr His Asp His Val Ser Val Arg | |
|                      45              50              55 | |
| ggc att cgc ctc cat tta gca gag gca ggc tcc ccc acc aaa ccc ctg | 546 |
| Gly Ile Arg Leu His Leu Ala Glu Ala Gly Ser Pro Thr Lys Pro Leu | |
| 60              65              70 | |
| gtt ctt ctg atc cac ggg gct ttc ggc ggt tgg tac gac tac cgc gaa | 594 |
| Val Leu Leu Ile His Gly Ala Phe Gly Gly Trp Tyr Asp Tyr Arg Glu | |
|                75              80              85 | |
| gtc atc ggc cca ctc gca gat gcc ggc ttc cac gtc gcc gcc atc gat | 642 |
| Val Ile Gly Pro Leu Ala Asp Ala Gly Phe His Val Ala Ala Ile Asp | |
| 90              95              100              105 | |
| cta cgc ggc tac ggc atg tcc gac aaa ccc cca aca ggc tac gac ctc | 690 |
| Leu Arg Gly Tyr Gly Met Ser Asp Lys Pro Pro Thr Gly Tyr Asp Leu | |
|                     110              115              120 | |
| cgc cac gca gcc gga gaa ctc agc agc gtt atc gca gct ctc ggc cac | 738 |
| Arg His Ala Ala Gly Glu Leu Ser Ser Val Ile Ala Ala Leu Gly His | |
|                         125              130              135 | |
| gat gac gca ctt ctt gtc ggc tcc gac acc ggc gcc agc atc gcc tgg | 786 |
| Asp Asp Ala Leu Leu Val Gly Ser Asp Thr Gly Ala Ser Ile Ala Trp | |
| 140              145              150 | |
| gct atc gct tcc atg tac ccc gaa cgg gtc cgc ggc cta att tcc ctc | 834 |
| Ala Ile Ala Ser Met Tyr Pro Glu Arg Val Arg Gly Leu Ile Ser Leu | |
|                155              160              165 | |
| ggc gcg atc cac ccc ctt gac atg cga cgc gcc atc cga cga aaa ccc | 882 |
| Gly Ala Ile His Pro Leu Asp Met Arg Arg Ala Ile Arg Arg Lys Pro | |
| 170              175              180              185 | |
| cac cta cac gtc tct gac ctc agc cga ctt gct cct ttt cgg ttg ccc | 930 |

-continued

```
His Leu His Val Ser Asp Leu Ser Arg Leu Ala Pro Phe Arg Leu Pro
            190                 195                 200 tca ttc ctg cat aac ctc ttc cac ttc gga atc acc agc gaa gct cga      978
Ser Phe Leu His Asn Leu Phe His Phe Gly Ile Thr Ser Glu Ala Arg
        205                 210                 215 cgt gag atc gtc aac aac acg tgc tcg tcc tac cag cgc agc aac gca      1026
Arg Glu Ile Val Asn Asn Thr Cys Ser Ser Tyr Gln Arg Ser Asn Ala
            220                 225                 230 ttc aca gag aca gtg ctc ctc cgc aaa aaa gca cta tcg atc gac cac      1074
Phe Thr Glu Thr Val Leu Leu Arg Lys Lys Ala Leu Ser Ile Asp His
        235                 240                 245 acc atc acc ccg atc atc cgc acc aac cgc tac ctc gtt ggg tcg atc      1122
Thr Ile Thr Pro Ile Ile Arg Thr Asn Arg Tyr Leu Val Gly Ser Ile
250                 255                 260                 265 ccc agc aaa aca gtc tcc gca ccg gtg tgg ctg ctc aga acc aac act      1170
Pro Ser Lys Thr Val Ser Ala Pro Val Trp Leu Leu Arg Thr Asn Thr
                270                 275                 280 cga cgc tgg gaa cat cta gcc aat act gcg cgc act cga acg aca ggg      1218
Arg Arg Trp Glu His Leu Ala Asn Thr Ala Arg Thr Arg Thr Thr Gly
            285                 290                 295 cca ttc acc acc atc gcg atc ccc ggc ggc tac gaa ctc ccc tac ctc      1266
Pro Phe Thr Thr Ile Ala Ile Pro Gly Gly Tyr Glu Leu Pro Tyr Leu
        300                 305                 310 gag aac cct tcc gaa ttt gca gca acc atc gca gag ttc gcg cgc acc      1314
Glu Asn Pro Ser Glu Phe Ala Ala Thr Ile Ala Glu Phe Ala Arg Thr
    315                 320                 325 acg ttt taagcactgt ggctgaggcg ctgctgctca tttggcgtca gaaggtcgca       1370
Thr Phe
330 tgattttggc gtgaattagt ggttttccc tggttttacc ccggcgcatt gaccggacca    1430 gacaggcgtg acaagaatca agattttcgc caggttttgt cacgtgtgtc tggtttgagc    1490 gactcgaaac caaacaggcg tgccaaaact tagatgtttt agcaatttt gtcacgtgtg     1550 tctggtttca tctagttcga ccgcaaacct cacggatttc ccctagtca ctcaaaaacc     1610 aaaactccct atatgcccct ctaagcgctt gggattcccc gacccatacc aatagacacc    1670 tctcctattc caggcccta aaacgccaca caggattggg cgtatctatc tcggattggg     1730 cgattcactg ccaagaccaa accacactgc ccacgcaacg gaaaaaccgc aatcgtgggc    1790 atctgtgacc ggttccgagc ccccaaaacc aaaccacact gcccacgcaa cggaaaaaac    1850 gcaatcgtgg gcatccctgt ctggtcctag ctcccgacga ctaagaaacc gcgcactgca    1910 tcgtatcgac aggctgagtc agcgcggtga tgtcgccgat ccgctcctgt acctcttcgg    1970 cagtgagaac gtaaccggta tcggagccgt c                                   2001
```

<210> SEQ ID NO 4
<211> LENGTH: 331
<212> TYPE: PRT
<213> ORGANISM: Corynebacterium glutamicum

<400> SEQUENCE: 4

```
Met Ala Phe Phe Ser Phe Ser Thr Ser Pro Leu Thr Arg Leu Ile Pro
1               5                   10                  15

Gly Ser Arg Ser Lys Ala Thr Gly Ala Lys Arg Arg Leu Ser Ser Thr
            20                  25                  30

Ile Ala Ser Ile Glu Arg Ser Pro Gly Ile Ile Ala Leu Asp Gly Pro
        35                  40                  45

Phe Thr His Asp His Val Ser Val Arg Gly Ile Arg Leu His Leu Ala
```

```
                50                  55                  60
Glu Ala Gly Ser Pro Thr Lys Pro Leu Val Leu Leu Ile His Gly Ala
 65                  70                  75                  80

Phe Gly Gly Trp Tyr Asp Tyr Arg Glu Val Ile Gly Pro Leu Ala Asp
                 85                  90                  95

Ala Gly Phe His Val Ala Ala Ile Asp Leu Arg Gly Tyr Gly Met Ser
                100                 105                 110

Asp Lys Pro Pro Thr Gly Tyr Asp Leu Arg His Ala Ala Gly Glu Leu
                115                 120                 125

Ser Ser Val Ile Ala Ala Leu Gly His Asp Asp Ala Leu Leu Val Gly
130                 135                 140

Ser Asp Thr Gly Ala Ser Ile Ala Trp Ala Ile Ala Ser Met Tyr Pro
145                 150                 155                 160

Glu Arg Val Arg Gly Leu Ile Ser Leu Gly Ala Ile His Pro Leu Asp
                165                 170                 175

Met Arg Arg Ala Ile Arg Arg Lys Pro His Leu His Val Ser Asp Leu
                180                 185                 190

Ser Arg Leu Ala Pro Phe Arg Leu Pro Ser Phe Leu His Asn Leu Phe
                195                 200                 205

His Phe Gly Ile Thr Ser Glu Ala Arg Arg Glu Ile Val Asn Asn Thr
210                 215                 220

Cys Ser Ser Tyr Gln Arg Ser Asn Ala Phe Thr Glu Thr Val Leu Leu
225                 230                 235                 240

Arg Lys Lys Ala Leu Ser Ile Asp His Thr Ile Thr Pro Ile Ile Arg
                245                 250                 255

Thr Asn Arg Tyr Leu Val Gly Ser Ile Pro Ser Lys Thr Val Ser Ala
                260                 265                 270

Pro Val Trp Leu Leu Arg Thr Asn Arg Arg Trp Glu His Leu Ala
                275                 280                 285

Asn Thr Ala Arg Thr Arg Thr Thr Gly Pro Phe Thr Thr Ile Ala Ile
                290                 295                 300

Pro Gly Gly Tyr Glu Leu Pro Tyr Leu Glu Asn Pro Ser Glu Phe Ala
305                 310                 315                 320

Ala Thr Ile Ala Glu Phe Ala Arg Thr Thr Phe
                325                 330

<210> SEQ ID NO 5
<211> LENGTH: 1266
<212> TYPE: DNA
<213> ORGANISM: Corynebacterium glutamicum ATCC13032
<220> FEATURE:
<221> NAME/KEY: CDS
<222> LOCATION: (1)..(1263)
<220> FEATURE:
<221> NAME/KEY: misc_feature
<222> LOCATION: (1264)..(1266)
<223> OTHER INFORMATION: taa stop codon

<400> SEQUENCE: 5 gtg gcc ctg gtc gta cag aaa tat ggc ggt tcc tcg ctt gag agt gcg      48
Met Ala Leu Val Val Gln Lys Tyr Gly Gly Ser Ser Leu Glu Ser Ala
 1               5                  10                  15 gaa cgc att aga aac gtc gct gaa cgg atc gtt gcc acc aag aag gct      96
Glu Arg Ile Arg Asn Val Ala Glu Arg Ile Val Ala Thr Lys Lys Ala
             20                  25                  30 gga aat gat gtc gtg gtt gtc tgc tcc gca atg gga gac acc acg gat     144
Gly Asn Asp Val Val Val Val Cys Ser Ala Met Gly Asp Thr Thr Asp
         35                  40                  45
```

```
gaa ctt cta gaa ctt gca gcg gca gtg aat ccc gtt ccg cca gct cgt      192
Glu Leu Leu Glu Leu Ala Ala Ala Val Asn Pro Val Pro Pro Ala Arg
 50              55                  60 gaa atg gat atg ctc ctg act gct ggt gag cgt att tct aac gct ctc      240
Glu Met Asp Met Leu Leu Thr Ala Gly Glu Arg Ile Ser Asn Ala Leu
 65              70                  75                  80 gtc gcc atg gct att gag tcc ctt ggc gca gaa gcc caa tct ttc acg      288
Val Ala Met Ala Ile Glu Ser Leu Gly Ala Glu Ala Gln Ser Phe Thr
                 85                  90                  95 ggc tct cag gct ggt gtg ctc acc acc gag cgc cac gga aac gca cgc      336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc      384
Ile Val Asp Val Thr Pro Gly Arg Val Arg Glu Ala Leu Asp Glu Gly
            115                 120                 125 aag atc tgc att gtt gct ggt ttc cag ggt gtt aat aaa gaa acc cgc      432
Lys Ile Cys Ile Val Ala Gly Phe Gln Gly Val Asn Lys Glu Thr Arg
130                 135                 140 gat gtc acc acg ttg ggt cgt ggt ggt tct gac acc act gca gtt gcg      480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt      528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag      576
Asp Gly Val Tyr Thr Ala Asp Pro Arg Ile Val Pro Asn Ala Gln Lys
                180                 185                 190 ctg gaa aag ctc agc ttc gaa gaa atg ctg gaa ctt gct gct gtt ggc      624
Leu Glu Lys Leu Ser Phe Glu Glu Met Leu Glu Leu Ala Ala Val Gly
            195                 200                 205 tcc aag att ttg gtg ctg cgc agt gtt gaa tac gct cgt gca ttc aat      672
Ser Lys Ile Leu Val Leu Arg Ser Val Glu Tyr Ala Arg Ala Phe Asn
            210                 215                 220 gtg cca ctt cgc gta cgc tcg tct tat agt aat gat ccc ggc act ttg      720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc      768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att      816
Gly Val Ala Thr Asp Lys Ser Glu Ala Lys Val Thr Val Leu Gly Ile
                260                 265                 270 tcc gat aag cca ggc gag gct gcg aag gtt ttc cgt gcg ttg gct gat      864
Ser Asp Lys Pro Gly Glu Ala Ala Lys Val Phe Arg Ala Leu Ala Asp
            275                 280                 285 gca gaa atc aac att gac atg gtt ctg cag aac gtc tct tct gta gaa      912
Ala Glu Ile Asn Ile Asp Met Val Leu Gln Asn Val Ser Ser Val Glu
            290                 295                 300 gac ggc acc acc gac atc acc ttc acc tgc cct cgt tcc gac ggc cgc      960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc     1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct     1056
Asn Val Leu Tyr Asp Asp Gln Val Gly Lys Val Ser Leu Val Gly Ala
                340                 345                 350 ggc atg aag tct cac cca ggt gtt acc gca gag ttc atg gaa gct ctg     1104
Gly Met Lys Ser His Pro Gly Val Thr Ala Glu Phe Met Glu Ala Leu
```

```
                     355                 360                 365
cgc gat gtc aac gtg aac atc gaa ttg att tcc acc tct gag att cgt    1152
Arg Asp Val Asn Val Asn Ile Glu Leu Ile Ser Thr Ser Glu Ile Arg
        370                 375                 380 att tcc gtg ctg atc cgt gaa gat gat ctg gat gct gct gca cgt gca    1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat    1248
Leu His Glu Gln Phe Gln Leu Gly Gly Glu Asp Glu Ala Val Val Tyr
            405                 410                 415 gca ggc acc gga cgc taa                                            1266
Ala Gly Thr Gly Arg
            420

<210> SEQ ID NO 6
<211> LENGTH: 421
<212> TYPE: PRT
<213> ORGANISM: Corynebacterium glutamicum ATCC13032

<400> SEQUENCE: 6

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285
```

Ala Glu Ile Asn Ile Asp Met Val Leu Gln Asn Val Ser Ser Val Glu
        290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
            325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Arg Ala
385                 390                 395                 400

Leu His Glu Gln Phe Gln Leu Gly Gly Glu Asp Glu Ala Val Val Tyr
            405                 410                 415

Ala Gly Thr Gly Arg
        420

<210> SEQ ID NO 7
<211> LENGTH: 1531
<212> TYPE: DNA
<213> ORGANISM: artificial sequence
<220> FEATURE:
<223> OTHER INFORMATION: polynucleotide encoding a variant of NCgl0292
<220> FEATURE:
<221> NAME/KEY: misc_feature
<222> LOCATION: (16)..(23)
<223> OTHER INFORMATION: recognition site for restriction endonuclease
      SbfI
<220> FEATURE:
<221> NAME/KEY: misc_feature
<222> LOCATION: (24)..(24)
<223> OTHER INFORMATION: nucleobase thymine (t) corresponds to position
      261 of SEQ ID NO:3
<220> FEATURE:
<221> NAME/KEY: CDS
<222> LOCATION: (91)..(1083)
<220> FEATURE:
<221> NAME/KEY: misc_feature
<222> LOCATION: (763)..(765)
<223> OTHER INFORMATION: tgc codon for cysteine
<220> FEATURE:
<221> NAME/KEY: mutation
<222> LOCATION: (764)..(764)
<223> OTHER INFORMATION: nucleobase guanine
<220> FEATURE:
<221> NAME/KEY: misc_feature
<222> LOCATION: (1084)..(1086)
<223> OTHER INFORMATION: taa stop codon
<220> FEATURE:
<221> NAME/KEY: misc_feature
<222> LOCATION: (1510)..(1515)
<223> OTHER INFORMATION: recognition site for restriction endonclease
      XmaI
<220> FEATURE:
<221> NAME/KEY: misc_feature
<222> LOCATION: (1511)..(1511)
<223> OTHER INFORMATION: nucleobase cytosine (c); corresponds to
      position 1748 of SEQ ID NO:3

<400> SEQUENCE: 7
tgccaagctt gcatgcctgc aggtctacac ctccgcgtcc ttccacagcc ccggcgccat      60
cactggcgac cactaaaaaa ggagacttcg atg gcc ttt ttt agc ttt tcg acg     114
                                Met Ala Phe Phe Ser Phe Ser Thr
                                 1               5

| | | |
|---|---|---|
| tct ccc ctc acc cgc ctc atc ccc ggc agc cgc tcc aaa gcc aca ggc<br>Ser Pro Leu Thr Arg Leu Ile Pro Gly Ser Arg Ser Lys Ala Thr Gly<br>10                      15                     20 | | 162 |
| gcc aaa cgg cgc ctg agc agc aca atc gcg tcg att gaa cgc tcc ccc<br>Ala Lys Arg Arg Leu Ser Ser Thr Ile Ala Ser Ile Glu Arg Ser Pro<br>25                     30                  35                 40 | | 210 |
| ggc atc att gcc cta gac gga ccg ttc acc cac gat cac gtc tcc gta<br>Gly Ile Ile Ala Leu Asp Gly Pro Phe Thr His Asp His Val Ser Val<br>                     45                     50                     55 | | 258 |
| cgt ggc att cgc ctc cat tta gca gag gca ggc tcc ccc acc aaa ccc<br>Arg Gly Ile Arg Leu His Leu Ala Glu Ala Gly Ser Pro Thr Lys Pro<br>                     60                     65                     70 | | 306 |
| ctg gtt ctt ctg atc cac ggg gct ttc ggc ggt tgg tac gac tac cgc<br>Leu Val Leu Leu Ile His Gly Ala Phe Gly Gly Trp Tyr Asp Tyr Arg<br>               75                     80                     85 | | 354 |
| gaa gtc atc ggc cca ctc gca gat gcc ggc ttc cac gtc gcc gcc atc<br>Glu Val Ile Gly Pro Leu Ala Asp Ala Gly Phe His Val Ala Ala Ile<br>90                     95                     100 | | 402 |
| gat cta cgc ggc tac ggc atg tcc gac aaa ccc cca aca ggc tac gac<br>Asp Leu Arg Gly Tyr Gly Met Ser Asp Lys Pro Pro Thr Gly Tyr Asp<br>105                   110                 115                120 | | 450 |
| ctc cgc cac gca gcc gga gaa ctc agc agc gtt atc gca gct ctc ggc<br>Leu Arg His Ala Ala Gly Glu Leu Ser Ser Val Ile Ala Ala Leu Gly<br>                    125                 130                135 | | 498 |
| cac gat gac gca ctt ctt gtc ggc tcc gac acc ggc gcc agc atc gcc<br>His Asp Asp Ala Leu Leu Val Gly Ser Asp Thr Gly Ala Ser Ile Ala<br>              140                     145                150 | | 546 |
| tgg gct atc gct tcc atg tac ccc gaa cgg gtc cgc ggc cta att tcc<br>Trp Ala Ile Ala Ser Met Tyr Pro Glu Arg Val Arg Gly Leu Ile Ser<br>                    155                 160                   165 | | 594 |
| ctc ggc gcg atc cac ccc ctt gac atg cga cgc gcc atc cga cga aaa<br>Leu Gly Ala Ile His Pro Leu Asp Met Arg Arg Ala Ile Arg Arg Lys<br>170                   175                 180 | | 642 |
| ccc cac cta cac gtc tct gac ctc agc cga ctt gct cct ttt cgg ttg<br>Pro His Leu His Val Ser Asp Leu Ser Arg Leu Ala Pro Phe Arg Leu<br>185                   190                 195                200 | | 690 |
| ccc tca ttc ctg cat aac ctc ttc cac ttc gga atc acc agc gaa gct<br>Pro Ser Phe Leu His Asn Leu Phe His Phe Gly Ile Thr Ser Glu Ala<br>                    205                 210                215 | | 738 |
| cga cgt gag atc gtc aac aac acg tgc tcg tcc tac cag cgc agc aac<br>Arg Arg Glu Ile Val Asn Asn Thr Cys Ser Ser Tyr Gln Arg Ser Asn<br>              220                     225                230 | | 786 |
| gca ttc aca gag aca gtg ctc ctc cgc aaa aaa gca cta tcg atc gac<br>Ala Phe Thr Glu Thr Val Leu Leu Arg Lys Lys Ala Leu Ser Ile Asp<br>235                   240                 245 | | 834 |
| cac acc atc acc ccg atc atc cgc acc aac cgc tac ctc gtt ggg tcg<br>His Thr Ile Thr Pro Ile Ile Arg Thr Asn Arg Tyr Leu Val Gly Ser<br>250                   255                 260 | | 882 |
| atc ccc agc aaa aca gtc tcc gca ccg gtg tgg ctg ctc aga acc aac<br>Ile Pro Ser Lys Thr Val Ser Ala Pro Val Trp Leu Leu Arg Thr Asn<br>265                   270                 275                280 | | 930 |
| act cga cgc tgg gaa cat cta gcc aat act gcg cgc act cga acg aca<br>Thr Arg Arg Trp Glu His Leu Ala Asn Thr Ala Arg Thr Arg Thr Thr<br>                    285                 290                295 | | 978 |
| ggg cca ttc acc acc atc gcg atc ccc ggc ggc tac gaa ctc ccc tac<br>Gly Pro Phe Thr Thr Ile Ala Ile Pro Gly Gly Tyr Glu Leu Pro Tyr<br>                    300                 305                310 | | 1026 |
| ctc gag aac cct tcc gaa ttt gca gca acc atc gca gag ttc gcg cgc<br>Leu Glu Asn Pro Ser Glu Phe Ala Ala Thr Ile Ala Glu Phe Ala Arg<br>315                   320                 325 | | 1074 |

```
acc acg ttt taagcactgt ggctgaggcg ctgctgctca tttggcgtca      1123
Thr Thr Phe
    330 gaaggtcgca tgattttggc gtgaattagt ggttttccc tggttttacc ccggcgcatt   1183 gaccggacca gacaggcgtg acaagaatca agatttcgc caggttttgt cacgtgtgtc   1243 tggtttgagc gactcgaaac caaacaggcg tgccaaaact tagatgtttt agcaatttt    1303 gtcacgtgtg tctggtttca tctagttcga ccgcaaacct cacggatttc ccctagtca    1363 ctcaaaaacc aaaactccct atatgccct ctaagcgctt gggattcccc gacccatacc   1423 aatagacacc tctcctattc caggcccta aaacgccaca caggattggt cgtatctatc    1483 tcggattggg cgattcactg ccaagacccg ggtaccgagc tcgaattc               1531

<210> SEQ ID NO 8
<211> LENGTH: 331
<212> TYPE: PRT
<213> ORGANISM: artificial sequence
<220> FEATURE:
<223> OTHER INFORMATION: Synthetic Construct

<400> SEQUENCE: 8

Met Ala Phe Phe Ser Phe Ser Thr Ser Pro Leu Thr Arg Leu Ile Pro
1               5                   10                  15

Gly Ser Arg Ser Lys Ala Thr Gly Ala Lys Arg Arg Leu Ser Ser Thr
            20                  25                  30

Ile Ala Ser Ile Glu Arg Ser Pro Gly Ile Ile Ala Leu Asp Gly Pro
        35                  40                  45

Phe Thr His Asp His Val Ser Val Arg Gly Ile Arg Leu His Leu Ala
    50                  55                  60

Glu Ala Gly Ser Pro Thr Lys Pro Leu Val Leu Ile His Gly Ala
65                  70                  75                  80

Phe Gly Gly Trp Tyr Asp Tyr Arg Glu Val Ile Gly Pro Leu Ala Asp
                85                  90                  95

Ala Gly Phe His Val Ala Ala Ile Asp Leu Arg Gly Tyr Gly Met Ser
            100                 105                 110

Asp Lys Pro Pro Thr Gly Tyr Asp Leu Arg His Ala Ala Gly Glu Leu
        115                 120                 125

Ser Ser Val Ile Ala Ala Leu Gly His Asp Asp Ala Leu Leu Val Gly
    130                 135                 140

Ser Asp Thr Gly Ala Ser Ile Ala Trp Ala Ile Ala Ser Met Tyr Pro
145                 150                 155                 160

Glu Arg Val Arg Gly Leu Ile Ser Leu Gly Ala Ile His Pro Leu Asp
                165                 170                 175

Met Arg Arg Ala Ile Arg Arg Lys Pro His Leu His Val Ser Asp Leu
            180                 185                 190

Ser Arg Leu Ala Pro Phe Arg Leu Pro Ser Phe Leu His Asn Leu Phe
        195                 200                 205

His Phe Gly Ile Thr Ser Glu Ala Arg Arg Glu Ile Val Asn Asn Thr
    210                 215                 220

Cys Ser Ser Tyr Gln Arg Ser Asn Ala Phe Thr Glu Thr Val Leu Leu
225                 230                 235                 240

Arg Lys Lys Ala Leu Ser Ile Asp His Thr Ile Thr Pro Ile Ile Arg
                245                 250                 255

Thr Asn Arg Tyr Leu Val Gly Ser Ile Pro Ser Lys Thr Val Ser Ala
            260                 265                 270
```

```
Pro Val Trp Leu Leu Arg Thr Asn Thr Arg Arg Trp Glu His Leu Ala
        275                 280                 285

Asn Thr Ala Arg Thr Arg Thr Thr Gly Pro Phe Thr Thr Ile Ala Ile
    290                 295                 300

Pro Gly Gly Tyr Glu Leu Pro Tyr Leu Glu Asn Pro Ser Glu Phe Ala
305                 310                 315                 320

Ala Thr Ile Ala Glu Phe Ala Arg Thr Thr Phe
                325                 330

<210> SEQ ID NO 9
<211> LENGTH: 20
<212> TYPE: DNA
<213> ORGANISM: artificial sequence
<220> FEATURE:
<223> OTHER INFORMATION: primer NCgl0292_fw

<400> SEQUENCE: 9
caacgaggta gcggttggtg                                                   20

<210> SEQ ID NO 10
<211> LENGTH: 20
<212> TYPE: DNA
<213> ORGANISM: artificial sequence
<220> FEATURE:
<223> OTHER INFORMATION: primer NCgl0292_rev

<400> SEQUENCE: 10
tccgcggcct aatttccctc                                                   20

<210> SEQ ID NO 11
<211> LENGTH: 20
<212> TYPE: DNA
<213> ORGANISM: artificial sequence
<220> FEATURE:
<223> OTHER INFORMATION: probe NCgl0292_C

<400> SEQUENCE: 11
acaacacgtg ctcgtcctac                                                   20

<210> SEQ ID NO 12
<211> LENGTH: 35
<212> TYPE: DNA
<213> ORGANISM: artificial sequence
<220> FEATURE:
<223> OTHER INFORMATION: probe NCgl0292_A

<400> SEQUENCE: 12
ttcggaatca ccagcgaagc tcgacgtgag atcgt                                  35
```